: United States Patent  
Li et al.

(10) Patent No.: US 11,925,893 B2
(45) Date of Patent: Mar. 12, 2024

(54) DEVICE FOR SEPARATING SUB-MICRON PARTICLES IN THE AIR

(71) Applicant: BEIHANG UNIVERSITY, Beijing (CN)

(72) Inventors: Xiaodong Li, Beijing (CN); Jizhou Liu, Beijing (CN)

(73) Assignee: BEIHANG UNIVERSITY, Beijing (CN)

(*) Notice: Subject to any disclaimer, the term of this patent is extended or adjusted under 35 U.S.C. 154(b) by 419 days.

(21) Appl. No.: 17/424,471

(22) PCT Filed: Aug. 4, 2020

(86) PCT No.: PCT/CN2020/106702
§ 371 (c)(1),
(2) Date: Jul. 20, 2021

(87) PCT Pub. No.: WO2022/027210
PCT Pub. Date: Feb. 10, 2022

(65) Prior Publication Data
US 2022/0305426 A1 Sep. 29, 2022

(51) Int. Cl.
*B01D 49/00* (2006.01)
*A61M 1/36* (2006.01)
(Continued)

(52) U.S. Cl.
CPC ......... *B01D 49/006* (2013.01); *A61M 1/3678* (2014.02); *B01D 21/283* (2013.01);
(Continued)

(58) Field of Classification Search
CPC .. B01D 49/006; B01D 21/283; A61M 1/3678; B01J 19/10; B01L 2300/0861; B01L 2400/0439; C12N 13/00
See application file for complete search history.

(56) References Cited

U.S. PATENT DOCUMENTS 4,339,247 A * 7/1982 Faulkner ............ B01D 19/0078
96/175
6,332,541 B1 12/2001 Coakley et al. ................ 209/18
(Continued)

FOREIGN PATENT DOCUMENTS

CN 1110929 A 11/1995
CN 101060898 A 10/2007
(Continued)

*Primary Examiner* — Stephen Hobson
(74) *Attorney, Agent, or Firm* — Stein IP, LLC

(57) ABSTRACT

The present disclosure provides a device for separating sub-micron particles in the air, comprising a first separation channel, a second separation channel and a collection device which are connected in sequence, wherein each of the first separation channel and the second separation channel is of a rectangle structure with two open ends, the height $H_1$ of the first separation channel is greater than the height $H_2$ of the second separation channel, and each separation channel is provided with a vibration sound source and an antimicrobial coating layer. Based on the agglomeration theory of suspended particles in the air by ultrasonic standing waves, the device can aggregate sub-micron suspended particles flowing into each channel of the device on the upper and lower wall surfaces and the centerline of the channel, and sterilize the aggregated particles, thereby effectively removing the sub-micron suspended particles in the air.

9 Claims, 4 Drawing Sheets

(51) Int. Cl.
  *B01D 21/28* (2006.01)
  *B01J 19/10* (2006.01)
  *C12N 13/00* (2006.01)

(52) U.S. Cl.
  CPC ........ *B01J 19/10* (2013.01); *B01L 2300/0861* (2013.01); *B01L 2400/0439* (2013.01); *C12N 13/00* (2013.01)

(56) References Cited

U.S. PATENT DOCUMENTS

| | | | |
|---|---|---|---|
| 8,134,705 B2* | 3/2012 | Kaduchak | G01N 15/1404 |
| | | | 356/337 |
| 8,387,803 B2* | 3/2013 | Thorslund | B01L 3/502761 |
| | | | 209/552 |
| 8,714,014 B2* | 5/2014 | Kaduchak | G01N 15/1404 |
| | | | 73/570.5 |
| 8,783,109 B2* | 7/2014 | Kaduchak | G01N 15/1459 |
| | | | 73/570.5 |
| 9,457,302 B2* | 10/2016 | Lipkens | C12M 47/02 |
| 9,675,902 B2* | 6/2017 | Lipkens | B01D 43/00 |
| 9,725,690 B2* | 8/2017 | Presz, Jr. | B01D 21/283 |
| 10,161,926 B2* | 12/2018 | Gilmanshin | G01N 15/1459 |
| 2022/0236138 A1* | 7/2022 | Li | G01H 13/00 |

FOREIGN PATENT DOCUMENTS

| | | |
|---|---|---|
| CN | 102026699 A | 4/2011 |
| CN | 102527488 A | 7/2012 |
| CN | 106853381 A | 6/2017 |
| CN | 109069966 A | 12/2018 |

* cited by examiner

DEVICE FOR SEPARATING SUB-MICRON PARTICLES IN THE AIR

CROSS-REFERENCE TO RELATED APPLICATIONS

This application is a national stage of International Application No. PCT/CN2020/106702, filed Aug. 4, 2020, in the International Patent Office, the disclosure of which is incorporated herein by reference.

TECHNICAL FIELD

The present disclosure relates to a device for separating sub-micron particles in the air, in particular to a device for separating sub-micron particles in the air by making use of ultrasonic standing waves, and more particularly to a device for separating suspended micro-pathogens (such as viruses) and nanoparticles in the air by making use of ultrasonic standing waves.

TECHNICAL BACKGROUND

Suspended particles in the air, such as pathogenic microorganisms and particulate matters PM2.5, are drawing increasing public concerns due to their harm to the human body. For particles larger than 1 μm in diameter, such as most big bacteria and PM2.5, filtration or inertial centrifugation can be used to separate them from the air. However, for sub-micron suspended particles such as viruses and nanoparticles, the aforementioned separation methods are less efficient due to the small size and good motion followability.

Generally, the size of viruses transmitted through human's respiratory passage is about 80 nm-300 nm. The viruses are often transmitted from infected patients through droplets generated by coughing or sneezing, forming sub-micron-sized aerosols in the air, which makes traditional filtering methods inefficient. In fact, the current air-conditioning systems in buildings (central or independent), the air control systems in means of transport (airplanes, railways and automobiles), the air purification devices, and the sewage systems (drainages and the like), all lack efficient, safe and convenient means to remove viruses within the sub-micron size range.

The literature (CN106853381A) discloses a particle separation device, the device comprising a liquid flow-through channel, a focused ultrasound device, and a separation ultrasound device, wherein the liquid flow-through channel includes a sample liquid inlet, a sheath liquid inlet, a focusing channel, a separation channel and at least two particle outlets. First ultrasonic waves generated by the focused ultrasound device act on the particles to be separated in the focusing channel, so that the particles move to the same plane perpendicular to the transmission direction of the first ultrasonic waves, and second ultrasonic waves generated by the separation ultrasound device act on the particles to be separated in the separation channel, so that particles of different sizes are separated to form different particle beams, thereby separating particles of different sizes. The device can effectively separate particles of different sizes to form different particle beams. However, since the carrier of the device is liquid, the particles are separated (aggregated) by means of high-frequency acoustic radiation pressure, which is not suitable for the separation of sub-micron suspended particles of sub-micron size formed in the air (that is, sub-micron suspended particles taking air as carrier). Therefore, there is an urgent need to provide a technical solution capable of effectively removing sub-micron particles in the air.

SUMMARY

Embodiments of the present disclosure provide a device for separating sub-micron particles in the air, which can effectively remove suspended sub-micron particles in the air based on the agglomeration theory of suspended particles in the air by ultrasonic standing waves.

The present disclosure adopts the technical solution:

Embodiments of the present disclosure provide a device for separating sub-micron particles in the air, comprising a first separation channel, a second separation channel and a collection device which are connected in sequence, wherein each of the first separation channel and the second separation channel is of a rectangle structure with two open ends, and the height $H_1$ of the first separation channel is greater than the height $H_2$ of the second separation channel;

by taking the leftmost end of the inner surface of the lower wall of the first separation channel as the origin of coordinates, the height direction of the first separation channel as the positive direction of the y axis, and the length direction of the first separation channel as the positive direction of the x axis, a coordinate system is constructed;

the outer surface of the upper wall of the first separation channel is provided with a first vibration sound source, and the inner surfaces of the upper wall and the lower wall are provided with a first antimicrobial coating layer; the first vibration sound source is used to generate a first standing wave field in the y direction, the first standing wave field is used to aggregate particles with a first diameter $d_{p1}$, and the first diameter $d_{p1}$ is ranged from 350 nm to 1.2 μm;

the outer surface of the upper wall of the second separation channel is provided with a second vibration sound source, and the inner surfaces of the upper wall and the lower wall are provided with a second antimicrobial coating layer; the second vibration sound source is used to generate a second standing wave field in the y direction, the second standing wave field is used to aggregate particles with a second diameter $d_{p2}$, and the second diameter $d_{p2}$ is ranged from 80 nm to 500 nm;

the relationship between a standing wave frequency $f_{a1}$ of the first standing wave field and the height $H_1$ is set such that particles flowing into the first separation channel are aggregated on the inner surface of the upper wall of the first separation channel, and the horizontal surface of the central axis in the y direction of the channel and the inner surface of the lower wall; and the first antimicrobial coating layer is used to adsorb particles aggregated on the inner surface of the upper wall and the inner surface of the lower wall of the first separation channel;

the relationship between a standing wave frequency $f_{a2}$ of the second standing wave field and the height $H_2$ is set such that particles flowing into the second separation channel are aggregated on the inner surface of the upper wall of the second separation channel, and the horizontal surface of the central axis in the y direction of the channel and the inner surface of the lower wall; and the second antimicrobial coating layer is used to adsorb particles aggregated on the inner surface of the upper wall and the inner surface of the lower wall of the second separation channel;

the relationship between the standing wave frequency of the first standing wave field and the standing wave frequency of the second standing wave field and the diameter of the corresponding aggregated particles is determined by the following formulas (1) to (4):

$$0.45 \leq 2\pi f_{a1} \tau_1 \leq 5.35 \quad (1)$$

$$\tau_1 = \rho_{mp} d_{p1}^2 / (18 \mu_g) \quad (2)$$

$$0.06 \leq 2\pi f_{a2} \tau_2 \leq 2.32 \quad (3)$$

$$\tau_2 \rho_{mp} d_{p2}^2 / (19 \mu_g) \quad (4)$$

where $\tau_1$ and $\tau_2$ represent relaxation time of the viscous force of the air in the first separation channel and the second separation channel respectively, $\rho_{mp}$ represents the material density of the particles, and $\mu_g$ represents the dynamic viscosity of air; and the collection device is used to collect particles aggregated on the central surface.

Based on the agglomeration theory of suspended particles in the air by ultrasonic standing waves, the device for separating sub-micron particles in the air provided by embodiments of the present disclosure can aggregate sub-micron suspended particles flowing into each channel of the device on the upper and lower wall surfaces and the centerline of the channel, and sterilize the aggregated particles, thereby effectively removing the sub-micron suspended particles in the air.

DETAILED DESCRIPTION

To make the technical problem to be solved, the technical solution and the advantages of the present disclosure more clear, the present disclosure will be further described below in detail in combination with the accompanying drawings and the specific embodiments.

Figure 1:
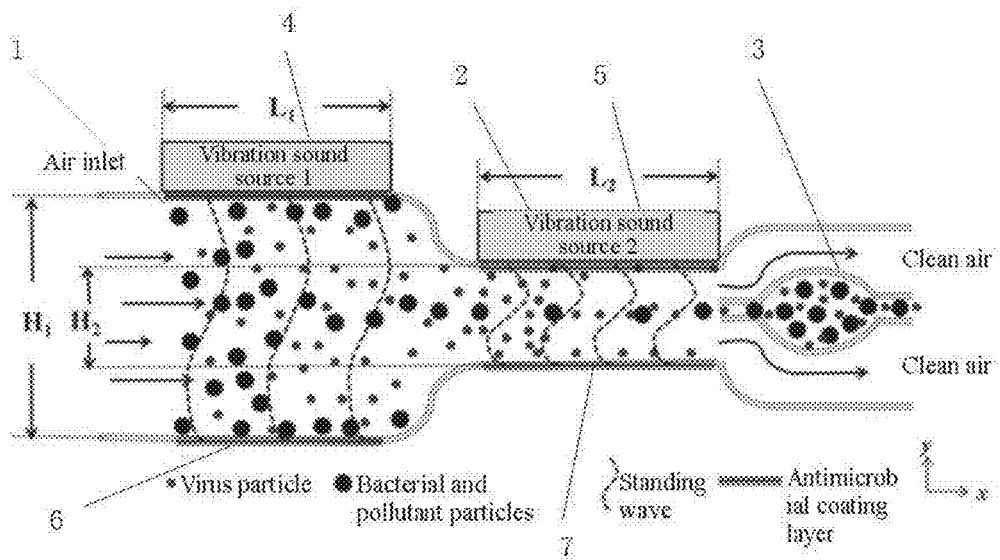
FIG. 1 is a structural schematic diagram of the device for separating sub-micron particles in the air provided by embodiments of the present disclosure.

As shown in FIG. 1, embodiments of the present disclosure provide a device for separating sub-micron particles in the air, comprising a first separation channel 1, a second separation channel 2 and a collection device 3 which are connected in sequence.

In embodiments of the present disclosure, each of the first separation channel 1 and the second separation channel 2 is of a rectangle structure with two open ends, wherein the height $H_1$ of the first separation channel 1 is greater than the height $H_2$ of the second separation channel 2. The first separation channel 1 is in sealing connection with the second separation channel 2, and in one example, the two are in smooth transition connection, so that the particle flow formed by the sub-micron particles flowing into the first separation channel 1 can smoothly flow into the second separation channel 2. The spacing between the first separation channel 1 and the second separation channel 2 is not specially limited, as long as the smooth inflow of the particle flow can be achieved. In a specific example, the spacing between the two may be 0.05 m. In addition, the separation channels may be made of anti-vibration material, such as steel material or the like.

In embodiments of the present disclosure, the outer surface of the upper wall of each separation channel is provided with a vibration sound source, and when the air flow entrained with sub-micron particles moves in the positive direction of the x axis at a mean velocity $U_{mean}$ and is introduced into the first separation channel 1 from the left side, a standing wave field is generated in the y direction when the first vibration sound source 4 operates, as shown in FIG. 1. In embodiments of the present disclosure, by taking the leftmost end of the inner surface of the lower wall of the first separation channel as the origin of coordinates, the height direction of the first separation channel as the positive direction of the y axis, and the length direction of the first separation channel as the positive direction of the x axis, a coordinate system is constructed. The vibration sound source may be a high-frequency vibration generator.

Specifically, the outer surface of the upper wall of the first separation channel 1 is provided with a first vibration sound source 4, and the inner surfaces of the upper wall and the lower wall are provided with a first antimicrobial coating layer 6; the first vibration sound source 4 is used to generate a first standing wave field in the y direction, the first standing wave field is used to aggregate particles with a first diameter $d_{p1}$, and the first diameter $d_{p1}$ is ranged from 350 nm to 1.2 μm, that is, the first separation channel 1 has a larger height and a lower standing wave frequency and is mainly responsible for aggregating sub-micron suspended particles with larger diameter, such as smaller bacterial particles. The outer surface of the upper wall of the second separation channel 2 is provided with a second vibration sound source 5, and the inner surfaces of the upper wall and the lower wall are provided with a second antimicrobial coating layer 7; the second vibration sound source 5 is used to generate a second standing wave field in the y direction, the second standing wave field is used to aggregate particles with a second diameter $d_{p2}$, and the second diameter $d_{p2}$ is ranged from 80 nm to 500 nm, that is, the second separation channel 2 has a smaller height and a higher standing wave frequency and is responsible for aggregating particles with smaller diameter, such as most virus particles. In this way, by means of the two standing wave fields, sub-micron particles with diameter within the range of 80 nm-1.2 μm in the air flow can be aggregated. Of course, if only for particles with diameter less than 500 nm or particles with diameter greater than 500 nm and less than 1.2 μm, it is possible to use either of the two separation channels.

The relationship between a standing wave frequency $f_{a1}$ of the first standing wave field and the height $H_1$ is set such that particles flowing into the first separation channel are aggregated on the inner surface of the upper wall of the first separation channel, and the horizontal surface of the central axis in the y direction of the channel and the inner surface of the lower wall. The relationship between a standing wave frequency $f_{a2}$ of the second standing wave field and the height $H_2$ is set such that particles flowing into the second separation channel are aggregated on the inner surface of the upper wall of the second separation channel, and the horizontal surface of the central axis in the y direction of the channel and the inner surface of the lower wall. That is, the particles flowing into the first separation channel may be aggregated at the position of $y=0$, $y=H_1/2$ and $y=H_1$ under the action of standing waves.

In a specific embodiment, the relationship between the standing wave frequency $f_{a1}$ of the first standing wave field and the height $H_1$ is: $f_{a1}*H_1=c_0$; and the relationship between the standing wave frequency $f_{a2}$ of the second standing wave field and the height $H_2$ is: $f_{a2}*H_2=c_0$, where $c_0$ represents the speed of sound in the air. In an example, the height of the first separation channel may be 2500 μm, the standing wave frequency of the first standing wave field may be 136000 Hz, the height of the second separation channel may be 1000 μm, and the standing wave frequency of the second standing wave field may be 340,000 Hz. The standing wave frequencies and channel heights shown in this example may be used to effectively aggregate sub-micron particles with diameter within the range of 80 nm-1.2 μm.

Further, in embodiments of the present disclosure, in order to efficiently separate the sub-micron particles, the relationship between the standing wave frequency of the first standing wave field and the standing wave frequency of the second standing wave field and the diameter of the corresponding aggregated particles is determined by the following formulas (1) to (4):

$$0.45 \leq 2\pi f_{a1}\tau_1 \leq 5.35 \quad (1)$$

$$\tau_1 = \rho_{mp} d_{p1}^2/(18\mu_g) \quad (2)$$

$$0.06 \leq 2\pi f_{a2}\tau_2 \leq 2.32 \quad (3)$$

$$\tau_2 = \rho_{mp} d_{p2}^2/(18\mu_g) \quad (4)$$

that is:

$$0.45 \leq 2\pi f_{a1}\rho_{mp} d_{p1}^2/(18\mu_g) \leq 5.35 \quad (5)$$

$$0.06 \leq 2\pi f_{a2}\rho_{mp} d_{p2}^2/(18\mu_g) \leq 2.32 \quad (6)$$

where $\tau_1$ and $\tau_2$ represent relaxation time of the viscous force of the air in the first separation channel and the second separation channel respectively, $\rho_{mp}$ represents the density of material constituting the particles, is obtained through actual measurement, and in one example, may be a density of 1400 kg/m³ close to the material density of viruses, bacteria and other particles in the air, and $\mu_g$ represents the dynamic viscosity of air. The inventor of the present disclosure found through verification of many experiments that when the standing wave frequency and particle diameter of the first separation channel satisfy the above formula (5), the effect of separating suspended particles with diameter within the range of 350 nm-1.2 μm from the carrier medium is relatively obvious, that is, the aggregating effect is good, especially when $2\pi f_{a1}\rho_{mp} d_{p1}^2/(18\mu_g)=1$, the greater the kinetic energy obtained by the suspended particles passing through the first separation channel from the carrier medium is, the easier it can be separated from the movement of the carrier medium, that is, the effect of aggregating the suspended particles is the best. Similarly, when the standing wave frequency and particle diameter of the second separation channel satisfy the above formula (6), the effect of separating suspended particles with diameter within the range of 80 nm-500 nm from the carrier medium is relatively obvious, that is, the aggregating effect is good, especially when $2\pi f_{a2}\rho_{mp} d_{p2}^2/(18\mu_g)=1$, the greater the kinetic energy obtained by the suspended particles passing through the second separation channel from the carrier medium is, the easier it can be separated from the movement of the carrier medium, that is, the effect of aggregating the suspended particles is the best.

In embodiments of the present disclosure, the first antimicrobial coating layer 6 is used to adsorb particles aggregated on the inner surface of the upper wall and the inner surface of the lower wall of the first separation channel, the second antimicrobial coating layer 7 is used to adsorb particles aggregated on the inner surface of the upper wall and the inner surface of the lower wall of the second separation channel, to attach and inactivate pathogenic micro-organism particles. The antimicrobial coating layers can be selected from the existing commercially available products, for example, Germagic long-acting disinfectant spray produced by Germagic Biological Technology (Shanghai) Limited.

In addition, the collection device 3 is used to collect particles aggregated on the central surface. The collection device 3 may be an existing device, which is not particularly limited in the present disclosure, as long as the aggregated suspended particles can be collected and post-processed. The clean air processed by the antimicrobial coating layers and collection device may normally flow out along the channel from other positions in the y direction and be discharged to such as atmosphere or be used normally.

In embodiments of the present disclosure, when the standing wave amplitude of a standing wave field is fixed, the length of a separation channel is positively correlated with the mean flow velocity of the particles flowing in the separation channel; when the mean flow velocity of the particles flowing in the separation channel is fixed, the length of the separation channel is negatively correlated with the standing wave amplitude of the standing wave field; and when the length of the separation channel is fixed, the standing wave amplitude of the standing wave field is positively correlated with the mean flow velocity of particles flowing in the separation channel. That is, when the standing wave amplitude of the first standing wave field is maintained unchanged, the length $L_1$ of the first separation channel 1 is positively correlated with the mean flow velocity $U_{mean1}$ of the particles flowing in the first separation channel 1; when the mean flow velocity of the particles flowing in the first separation channel is maintained unchanged, the length of the first separation channel is negatively correlated with the standing wave amplitude $p_1$ of the first standing wave field; and when the length of the first separation channel is maintained unchanged, the standing wave amplitude $p_1$ of the first standing wave field is positively correlated with the mean flow velocity $U_{mean1}$ of the particles flowing in the first separation channel. When the standing wave amplitude of the second standing wave field is maintained unchanged, the length $L_2$ of the second separation channel 2 is positively correlated with the mean flow velocity $U_{mean2}$ of the particles flowing in the second separation channel; when the mean flow velocity of the particles flowing in the second separation channel is maintained unchanged, the length of the second separation channel is negatively correlated with the standing wave amplitude $p_2$ of the second standing wave field; and when the length of the second separation channel is maintained unchanged, the standing wave amplitude $p_2$ of the second standing wave field is positively correlated with the mean flow velocity $U_{mean2}$ of the particles flowing in the second separation channel.

In a specific embodiment of the present disclosure, in order to effectively aggregate sub-micron particles with diameter within the range of 80 nm-1.2 μm in the air flow, the main parameters of the first separation channel 1 and the second separation channel 2 may be as shown in the following Table 1:

TABLE 1

Main Parameters of Separation Channel

| | | |
|---|---|---|
| First Separation Channel | Height $H_1$ | 2500 μm |
| | Length $L_1$ | 0.15 m-0.25 m |
| | Standing wave frequency $f_{a1}$ | 136000 Hz |
| | Mean flow velocity $U_{mean}$ | 0.05 m/s-0.08 m/s |
| | Standing wave amplitude $p_1$ | 1000 Pa or more |
| | Diameter range of aggregated particles (smallest best, largest) | (350 nm, 520 nm, 1.2 μm) |
| Second separation channel | Height $H_2$ | 1000 μm |
| | Length $L_2$ | 0.25 m-0.35 m |
| | Standing wave frequency $f_{a2}$ | 340000 Hz |
| | Mean flow velocity $U_{mean}$ | 0.125 m/s-0.2 m/s |
| | Standing wave amplitude $p_2$ | 1000 Pa or more |
| | Diameter range of aggregated particles (smallest, best, largest) | (80 nm, 320 nm, 500 nm) |

That is to say, in embodiments of the present disclosure, under the condition that the first separation channel has a length $L_1$=0.15-0.25 m and a height $H_1$=2500 μm, the high-frequency vibration generator has a frequency $f_{a1}$=136000 Hz, and the standing wave sound pressure amplitude $p_1$ generated exceeds 1000 Pa, the smallest diameter of the particles capable of being aggregated is 350 nm, the largest diameter of the particles capable of being aggregated is 1.2 μm, and the aggregating effect on the suspended particles with diameter of 520 nm is the best. Under the condition that the second separation channel has a length $L_2$=0.25-0.35 m and a height $H_2$=1000 μm, the high-frequency vibration generator has a frequency $f_{a2}$=340000 Hz, and the standing wave sound pressure amplitude $p_2$ generated exceeds 1000 Pa, the smallest diameter of the particles capable of being aggregated goes down to 80 nm, the largest diameter of the particles capable of being aggregated is 500 nm, and the aggregating effect on the suspended particles with diameter of 320 nm is the best, which can effectively cover the diameter range of most of airborne virus particles.

EMBODIMENTS

In embodiments of the present disclosure, the aggregating effects of the first separation channel and the second separation channel which have the parameters shown in the following Table 2 are verified.

TABLE 2

Simulation Parameters of Separation Channel

| | | |
|---|---|---|
| First Separation Channel | Channel height $H_1$ | 2500 μm |
| | Channel length $L_1$ | 0.2 m |
| | Standing wave frequency $f_{a1}$ | 136000 Hz |
| | Mean flow velocity $U_{mean}$ | 0.08 m/s |
| | Standing wave amplitude $p_1$ | 1000 Pa |
| | Diameters of aggregated particles | 350 nm, 520 nm, 750 nm, 1 μm and 1.2 μm |
| Second Separation Channel | Channel height $H_2$ | 1000 μm |
| | Channel length $L_2$ | 0.3 m |
| | Standing wave frequency $f_{a2}$ | 340000 Hz |
| | Mean flow velocity $U_{mean}$ | 0.2 m/s |
| | Standing wave amplitude $p_2$ | 1000 Pa |
| | Diameters of aggregated particles | 80 nm, 100 nm, 160 nm, 240 nm, 320 nm and 500 nm |

That is, in the simulation experiment, (1) for the first separation channel, simulating the aggregating process of particles with diameters of 350 nm, 520 nm, 750 nm, 1 μm and 1.2 μm is used to verify the aggregating effect thereof on particles with diameters greater than 500 nm and less than 1.2 μm; and (2) for the second separation channel, simulating the aggregating process of particles with diameters of 80 nm, 100 nm, 160 nm, 240 nm, 320 nm and 500 nm is used to verify the aggregating effect thereof on particles with diameter less than 500 nm. In addition, when the aggregating effect of the second separation channel is verified, the simulation process focuses on the aggregating effect on particles (airborne viruses) with diameter within the range of 80 nm-300 nm. The value of the material density $\rho_{mp}$ of the particles during simulation is 1400 kg/m³.

In embodiments of the present disclosure, the numerical simulation method defined by the following formulas (7)-(11) is used to verify the aggregating effects of the separation channels with the parameters shown in Table 2.

(Numerical Simulation Method)

A standing wave is as a driving factor for particle motion and is given by an analytical solution. Assuming that the wavelength of the standing wave is equal to the height H of the channel, the pressure $p_g(y, t)$ of the standing wave and the velocity in the y direction $v_g(y, t)$ are respectively expressed as:

$$p_g(y, t) = p_a \cos\left(\frac{2\pi}{H} y\right) \cos(2\pi f_a t) \quad (7)$$

$$v_g(y, t) = \frac{p_a}{\rho_a c_0} \sin\left(\frac{2\pi}{H} y\right) \sin(2\pi f_a t) \quad (8)$$

where t represents the time of action of the standing wave on the particles, that is, the standing wave action time, in s, which is determined by actual measurement; and y represents the coordinate of the particles in they direction at the standing wave action time t, which is determined by actual measurement;

the flow in the channel is assumed to be laminar flow under the condition that the mean flow velocity $U_{mean}$ is low. According to the Couette formula, the velocity profile distribution $U_g(y)$ of the time-averaged velocity in the y direction is expressed as:

$$U_g(y) = \frac{6 U_{mean}}{H^2}(H - y)y \quad (9)$$

the suspended sub-micron particles are regarded as moving spherical mass points; the Newtonian equations of motion thereof is:

$$\frac{dx'_p}{dt} = u_p^i \quad (10)$$

$$\frac{du'_p}{dt} = C_d(u_g^i - u_p^i)$$

where $x_p^i$ and $u_p^i$ represent the spatial position and velocity of the $i^{th}$ particle, respectively, $u_g^i$ represents the velocity of the air flow at the position of the $i^{th}$ particle, which is determined by the velocity $v_g(y, t)$ of the standing wave and the mean velocity $U_g(y)$ of the air flow, namely $u_g^i = v_g(y, t) + U_g(y)$. $C_d$ represents a coefficient of viscous force between the air medium and the particles, which is shown by the Stokes viscosity coefficient:

$$C_d = \begin{cases} \dfrac{18\mu}{\rho_{mp}d_p^2} & Re < 0.01 \\ \dfrac{18\mu}{\rho_{mp}d_p^2}\left(1 + 0.1315Re^{0.82-0.05\,log(Re)}\right) & 0.01 \leq Re < 20 \\ \dfrac{18\mu}{\rho_{mp}d_p^2}\left(1 + 0.1935Re^{0.6035}\right) & Re \geq 20 \end{cases} \quad (11)$$

In this way, according to the standing wave frequency $f_a$, standing wave pressure amplitude $p_a$, channel height H, mean flow velocity $U_{mean}$, particle diameter $d_p$ and particle material density $\rho_{mp}$ which are shown in the Table 2, the standing wave action time t measured during simulation and the coordinate y of the corresponding particles in they direction, based on the above formulas (7)-(11), the spatial position and velocity of each particle may be obtained. The simulation results may be shown in FIGS. 2(a)-(e) and FIGS. 3(a)-(f) respectively.

Figure 2:
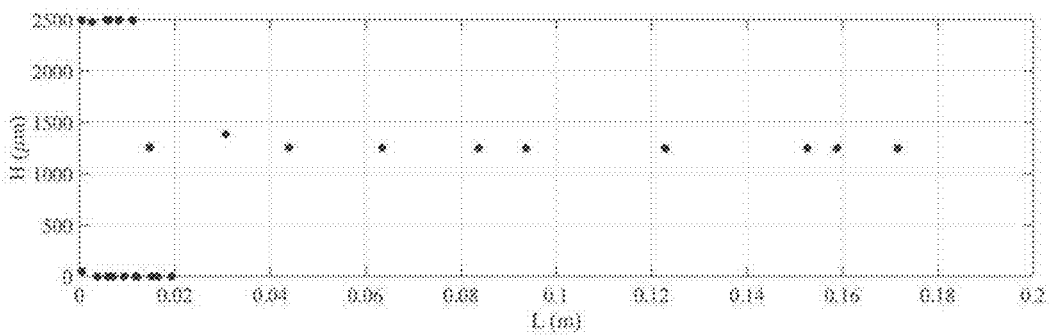
FIGS. 2(a)-2(e) show simulation results of simulating separation of sub-micron particles by the first separation channel according to embodiments of the present disclosure.
Figure 2:
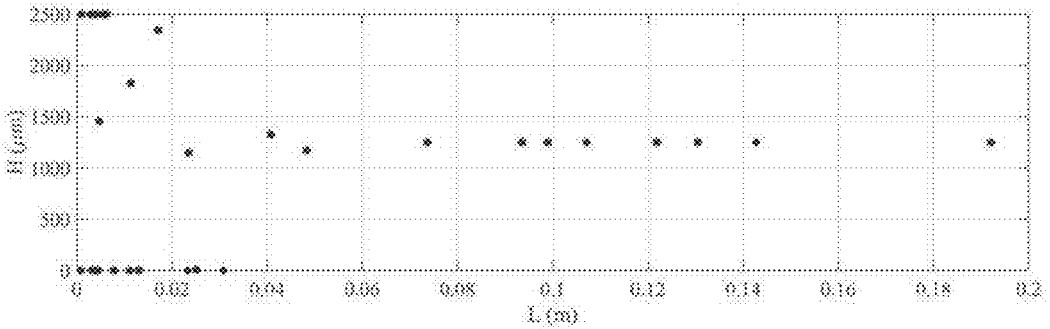
Figure 2:
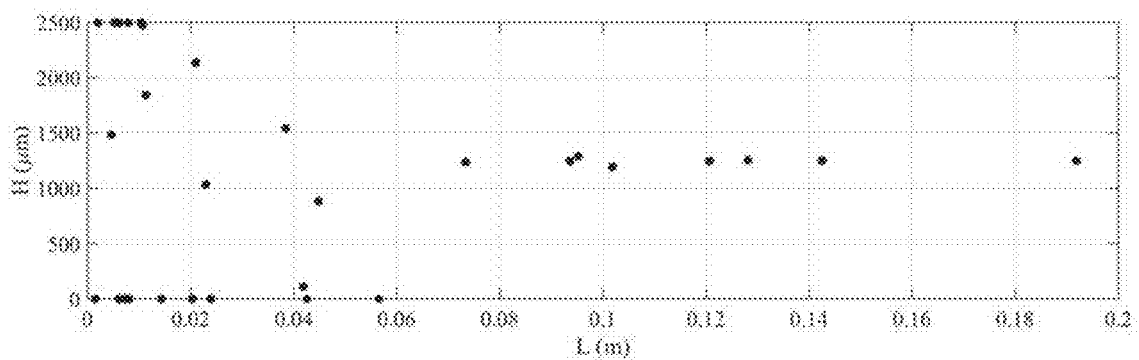
Figure 2:
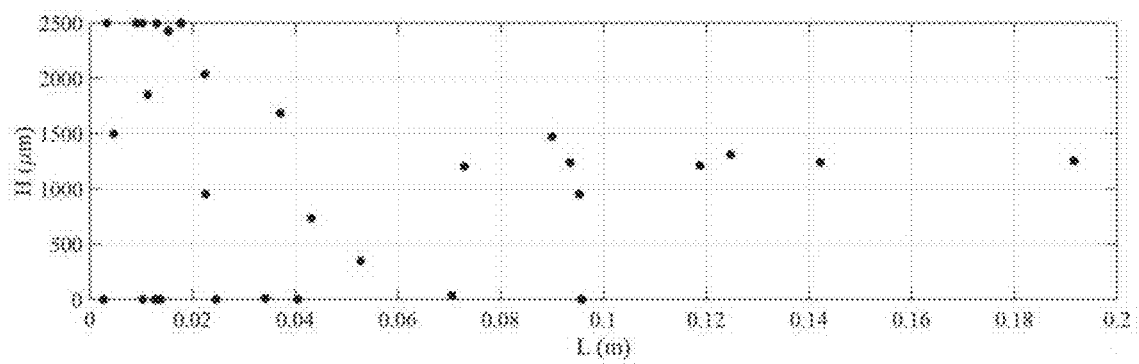
Figure 2:
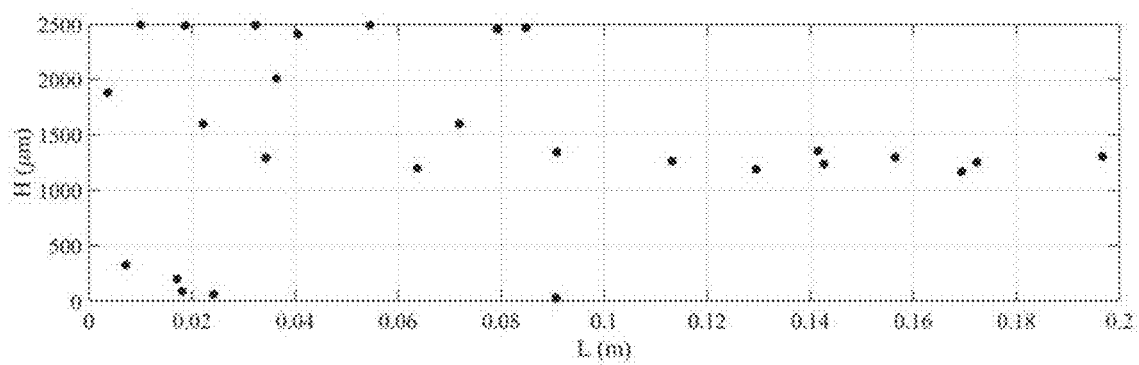

FIGS. 2(a)-(e) respectively show the distribution and state of particles with five diameters of 350 nm, 520 nm, 750 nm, 1 μm and 1.2 μm in the first separation channel after 3 seconds of standing wave action. As shown in FIGS. 2(a)-(c), this embodiment has a very obvious aggregating effect on particles with diameters of 350-750 nm. Most particles are aggregated in the theoretical positions y=0, y=H/2 and y=H after entering the channel for 0.1 m. For particles with diameters of 1 μm and 1.2 μm, as shown in FIG. 2(d) and FIG. 2(e), the standing wave has a slightly lower aggregating effect on same, however, when the particles move axially to the channel exit (0.15 m), the particles are basically aggregated in the theoretical positions, that is, on the inner surfaces of the two walls and centerline of the first separation channel.

Figure 3:
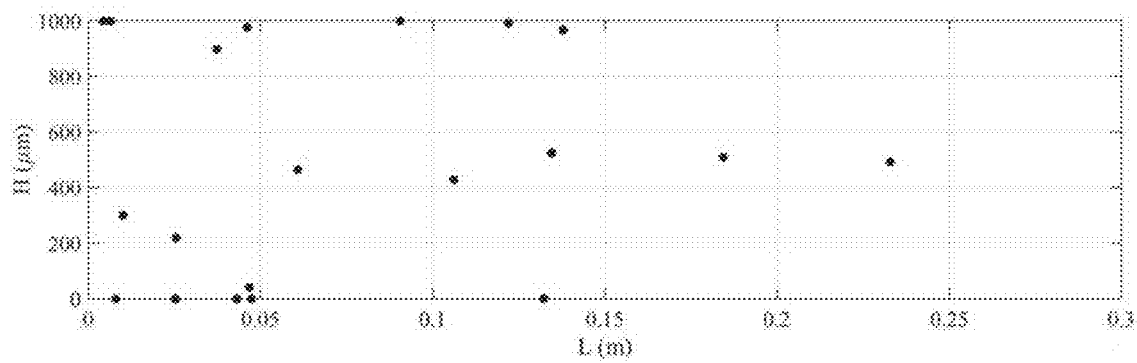
FIGS. 3(a)-3(f) show simulation results of simulating separation of sub-micron particles by the second separation channel according to embodiments of the present disclosure.
Figure 3:
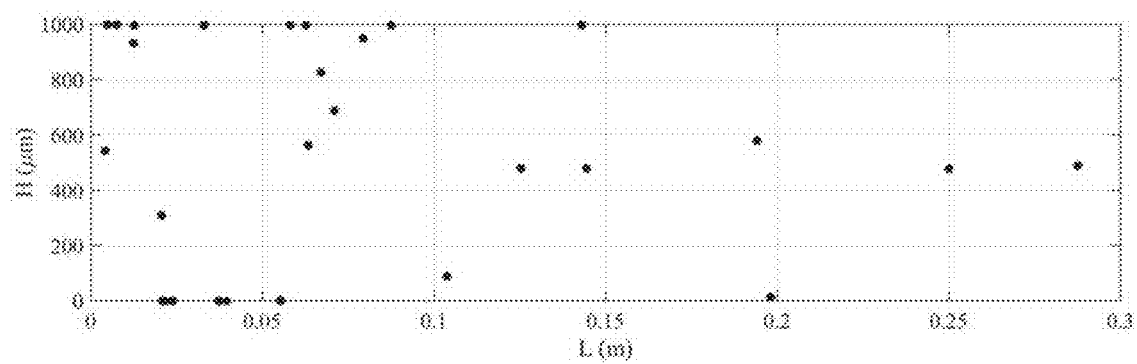
Figure 3:
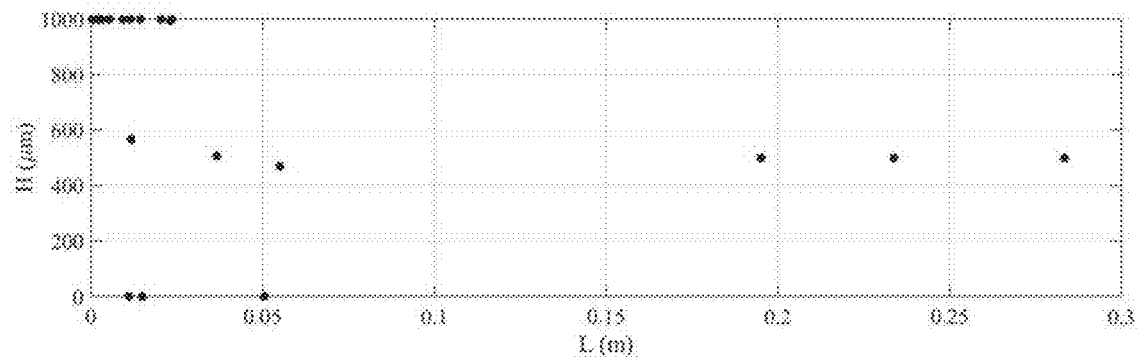
Figure 3:
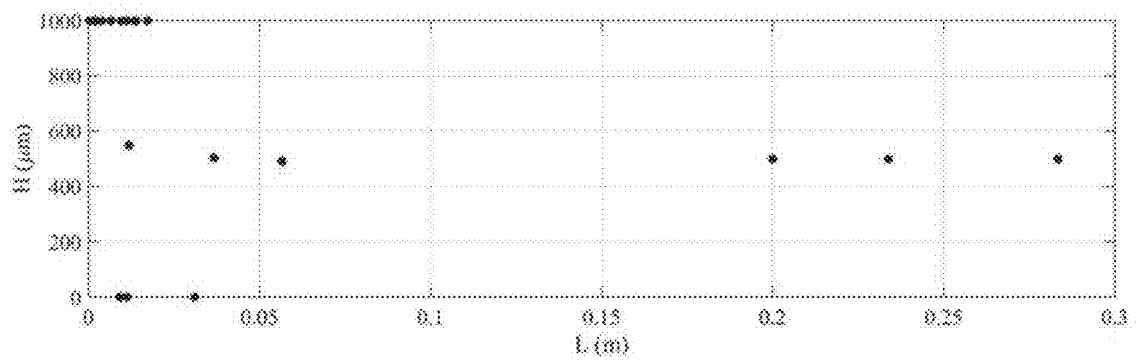
Figure 3:
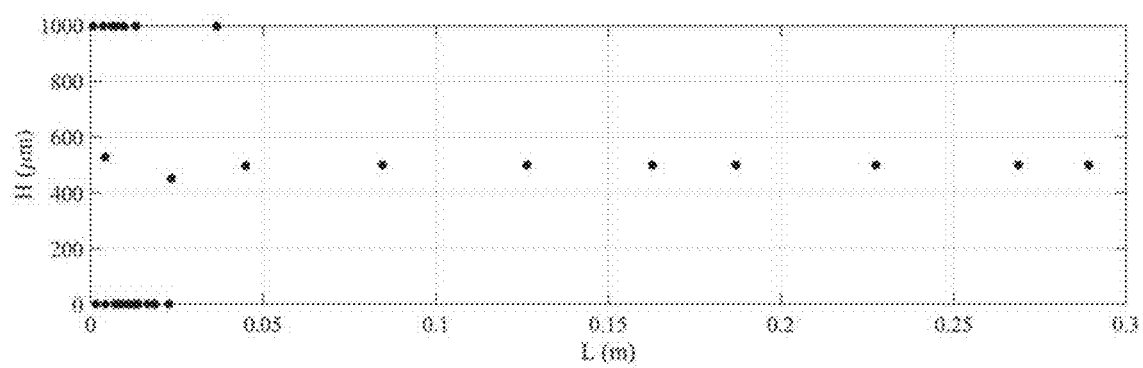
Figure 3:
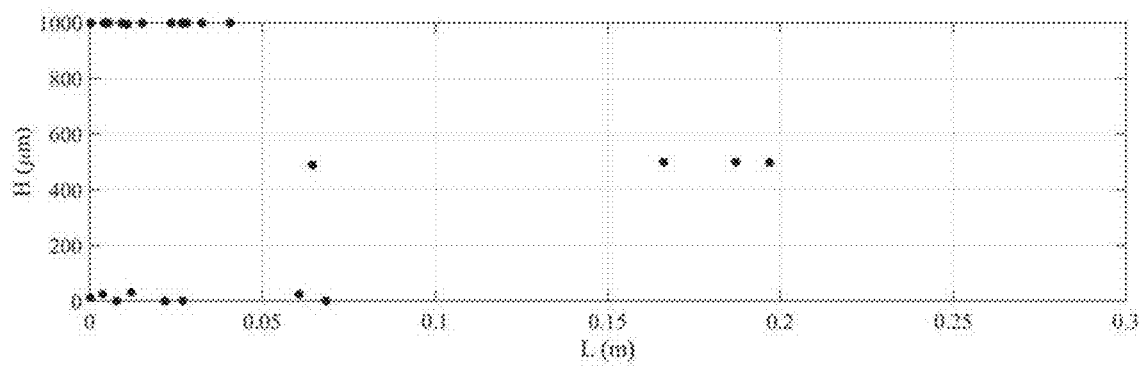

FIGS. 3(a)-(f) respectively show the distribution and state of particles with six diameters of 80 nm, 100 nm, 160 nm, 240 nm, 320 nm and 500 nmin the second separation channel after 3 seconds of standing wave action. As shown in FIG. 3(a), for particles with smaller diameter (for example, 80 nm), the standing wave has a slightly lower aggregating effect on same, however, when the particles move axially to the channel exit (0.25 m), the particles are basically aggregated in the theoretical positions, that is, on the inner surfaces of the two walls and centerline of the second separation channel. FIGS. 3(b)-(e) show the effect of the standing wave on the aggregating distribution of particles with diameter of 100 nm-320 nm. It can be seen that under the simulation scheme of this embodiment, particles within this diameter range can be aggregated in the theoretical positions before flowing out of the channel. This diameter range is also the size range of airborne epidemic viruses such as influenza viruses, coronaviruses, etc., thereby verifying the effectiveness of the simulation solution of this embodiment in removing infectious pathogens in the air flow. For particles with a diameter of 500 nm, FIG. 3(f) shows that the simulation scheme also has a good aggregating effect on same. Almost all particles may be quickly aggregated on the inner surfaces of the two walls and centerline of the channel after entering the channel for 0.1 m.

To sum up, based on the agglomeration theory of suspended particles in the air by ultrasonic standing waves, the device for separating sub-micron particles in the air provided by embodiments of the present disclosure can aggregate sub-micron suspended particles flowing into each channel of the device on the upper and lower wall surfaces and the centerline of the channel, and sterilize the aggregated particles, thereby effectively removing the sub-micron suspended particles in the air.

The above embodiments are only specific embodiments of the present disclosure used for describing the technical solution of the present disclosure rather than limiting the same, but the protection scope of the present disclosure is not limited thereto. Although the present disclosure is described in detail by referring to the above embodiments, those skilled in the art should understand that: those skilled in the art familiar with the technical field may still modify or easily contemplate to make changes to the technical solution recorded in the above embodiment, or equivalently replace some of the technical features within the technical range of the present disclosure; however, these amendments, changes or replacements do not enable the essence of the corresponding technical solution to depart from the spirit and the scope of the technical solution of embodiments of the present disclosure, and should be covered within the protection scope of the present disclosure. Therefore, the protection scope of the present disclosure should be determined by the protection scope of the claims.

The invention claimed is:

1. A device for separating sub-micron particles in the air, comprising: a first separation channel, a second separation channel and a collection device which are connected in sequence,
   wherein each of the first separation channel and the second separation channel is of a rectangle structure with two open ends, and the height $H_1$ of the first separation channel is greater than the height $H_2$ of the second separation channel;
   by taking the leftmost end of the inner surface of the lower wall of the first separation channel as the origin of coordinates, the height direction of the first separation channel as the positive direction of the y axis, and the length direction of the first separation channel as the positive direction of the x axis, a coordinate system is constructed;
   the outer surface of the upper wall of the first separation channel is provided with a first vibration sound source, and the inner surfaces of the upper wall and the lower wall are provided with a first antimicrobial coating layer; the first vibration sound source is used to generate a first standing wave field in the y direction, the first standing wave field is used to aggregate particles with a first diameter $d_{p1}$, and the first diameter $d_{p1}$ is ranged from 350 nm to 1.2 μm;
   the outer surface of the upper wall of the second separation channel is provided with a second vibration sound source, and the inner surfaces of the upper wall and the lower wall are provided with a second antimicrobial coating layer; the second vibration sound source is used to generate a second standing wave field in the y direction, the second standing wave field is used to aggregate particles with a second diameter $d_{p2}$, and the second diameter $d_{p2}$ is ranged from 80 nm to 500 nm;
   the relationship between a standing wave frequency $f_{a1}$ of the first standing wave field and the height $H_1$ is set such that particles flowing into the first separation channel are aggregated on the Inner surface of the upper wall of the first separation channel, and the horizontal surface of the central axis in the y direction of the channel and the inner surface of the lower wall; and the first antimicrobial coating layer is used to adsorb particles aggregated on the inner surface of the upper wall and the inner surface of the lower wall of the first separation channel;

the relationship between a standing wave frequency $f_{a2}$ of the second standing wave field and the height $H_2$ is set such that particles flowing into the second separation channel are aggregated on the inner surface of the upper wall of the second separation channel, and the horizontal surface of the central axis in the y direction of the channel and the inner surface of the lower wall; and the second antimicrobial coating layer is used to adsorb particles aggregated on the inner surface of the upper wall and the inner surface of the lower wall of the second separation channel;

the relationship between the standing wave frequency of the first standing wave field and the standing wave frequency of the second standing wave field and the diameter of the corresponding aggregated particles is determined by the following formulas (1) to (4):

$$0.45 \leq 2\pi f_{a1}\tau_1 \leq 5.35 \quad (1)$$

$$\tau_1=\rho_{mp}d_{p1}^{2}/(18\mu_g) \quad (2)$$

$$0.06 \leq 2\pi f_{a2}\tau_2 \leq 2.32 \quad (3)$$

$$\tau_2\rho_{mp}d_{p2}^{2}/(18\mu_g) \quad (4)$$

where $\tau_1$ and $\tau_2$ represent relaxation time of the viscous force of the air in the first separation channel and the second separation channel respectively, $\rho_{mp}$ represents the material density of the particles, and $\mu_g$ represents the dynamic viscosity of air; and the collection device is used to collect particles aggregated on the central surface.

2. The device for separating sub-micron particles in the air according to claim 1, wherein: the relationship between the standing wave frequency $f_{a1}$ of the first standing wave field and the height $H_1$ is: $f_{a1}*H_1=c_0$; and the relationship between the standing wave frequency $f_{a2}$ of the second standing wave field and the height $H_2$ is: $f_{a2}*H_2=c_0$;

where $c_0$ represents the speed of sound in the air.

3. The device for separating sub-micron particles in the air according to claim 1, wherein: the first separation channel has a height of 2500 μm, and the first standing wave field has a standing wave frequency of 136000 Hz; and the second separation channel has a height of 1000 μm, and the second standing wave field has a standing wave frequency of 340000 Hz.

4. The device for separating sub-micron particles in the air according to claim 1, wherein: the first separation channel is in smooth transition connection with the second separation channel.

5. The device for separating sub-micron particles in the air according to claim 1, wherein: when the standing wave amplitude of the first standing wave field is maintained unchanged, the length of the first separation channel is positively correlated with the mean flow velocity of the particles flowing in the first separation channel;

when the mean flow velocity of the particles flowing in the first separation channel is maintained unchanged, the length of the first separation channel is negatively correlated with the standing wave amplitude of the first standing wave field; and when the length of the first separation channel is maintained unchanged, the standing wave amplitude of the first standing wave field is positively correlated with the mean flow velocity of the particles flowing in the first separation channel.

6. The device for separating sub-micron particles in the air according to claim 5, wherein:

the mean flow velocity of the particles flowing in the first separation channel is 0.05 m/s-0.08 m/s;

the standing wave amplitude of the first standing wave field is greater than or equal to 1000 Pa; and the first separation channel has a length of 0.15 m-0.25 m.

7. The device for separating sub-micron particles in the air according to claim 1, wherein: when the standing wave amplitude of the second standing wave field is maintained unchanged, the length of the second separation channel is positively correlated with the mean flow velocity of the particles flowing in the second separation channel;

when the mean flow velocity of the particles flowing in the second separation channel is maintained unchanged, the length of the second separation channel is negatively correlated with the standing wave amplitude of the second standing wave field; and when the length of the second separation channel is maintained unchanged, the standing wave amplitude of the second standing wave field is positively correlated with the mean flow velocity of the particles flowing in the second separation channel.

8. The device for separating sub-micron particles in the air according to claim 7, wherein:

the mean flow velocity of particles flowing in the second separation channel is 0.125 m/s-0.2 m/s;

the standing wave amplitude of the second standing wave field is greater than or equal to 1000 Pa; and the second separation channel has a length of 0.25 m-0.35 m.

9. The device for separating sub-micron particles in the air according to claim 2, wherein: the first separation channel has a height of 2500 μm, and the first standing wave field has a standing wave frequency of 136000 Hz; and the second separation channel has a height of 1000 μm, and the second standing wave field has a standing wave frequency of 340000 Hz.

* * * * *